(12) United States Patent
Frezza et al.

(10) Patent No.: US 10,504,612 B2
(45) Date of Patent: Dec. 10, 2019

(54) POLYNUCLEOTIDE PROBE DESIGN

(71) Applicant: Emerald Therapeutics, Inc., Menlo Park, CA (US)

(72) Inventors: Brian M. Frezza, Redwood City, CA (US); Bradley M. Bond, Palo Alto, CA (US); Collin A. Melton, Menlo Park, CA (US); Catherine L. Hofler, San Francisco, CA (US); Daniel J. Kleinbaum, Redwood City, CA (US)

(73) Assignee: EMERALD THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 13/801,592

(22) Filed: Mar. 13, 2013

(65) Prior Publication Data

US 2013/0338015 A1    Dec. 19, 2013

Related U.S. Application Data

(60) Provisional application No. 61/660,145, filed on Jun. 15, 2012.

(51) Int. Cl.
*G16B 25/00* (2019.01)

(52) U.S. Cl.
CPC .................... *G16B 25/00* (2019.02)

(58) Field of Classification Search
CPC ........ G06F 19/20; C12Q 1/6813–6841; C12Q 2537/165
See application file for complete search history.

(56) References Cited

U.S. PATENT DOCUMENTS

| | | | |
|---|---|---|---|
| 6,238,927 | B1 | 5/2001 | Abrams et al. |
| 6,251,588 | B1* | 6/2001 | Shannon et al. ............ 435/6.18 |
| 6,448,387 | B1 | 9/2002 | Slater et al. |
| 7,501,253 | B2 | 3/2009 | Pourmand et al. |
| 7,538,202 | B2 | 5/2009 | Zhang et al. |
| 8,036,835 | B2 | 10/2011 | Sampas et al. |
| 2002/0119458 | A1 | 8/2002 | Suyama et al. |
| 2003/0152924 | A1 | 8/2003 | Ullman et al. |
| 2003/0236633 | A1* | 12/2003 | Mei .................. G06F 19/20 702/20 |
| 2004/0224345 | A1* | 11/2004 | Vandersall et al. ............. 435/6 |
| 2004/0259124 | A1* | 12/2004 | Bekiranov et al. ............. 435/6 |
| 2005/0075792 | A1 | 4/2005 | Shaprio et al. |
| 2005/0112065 | A1 | 5/2005 | Drummond et al. |
| 2007/0072215 | A1 | 3/2007 | Seelig et al. |
| 2007/0275389 | A1* | 11/2007 | De Witte et al. ............... 435/6 |
| 2008/0039339 | A1* | 2/2008 | Hassibi et al. ................ 506/9 |
| 2008/0269072 | A1 | 10/2008 | Hart et al. |
| 2009/0042735 | A1* | 2/2009 | Blair et al. .................... 506/9 |
| 2009/0170719 | A1 | 7/2009 | Kazakov et al. |
| 2009/0191546 | A1 | 7/2009 | Zhang et al. |
| 2011/0039735 | A1* | 2/2011 | Yamada et al. ............. 506/24 |
| 2012/0100633 | A1 | 4/2012 | Manetto et al. |

FOREIGN PATENT DOCUMENTS

| | | |
|---|---|---|
| EP | 1 889 924 A1 | 2/2008 |
| WO | WO 2008/097929 A2 | 8/2008 |

OTHER PUBLICATIONS

Dai, H., Meyer, M., Stepaniants, S., Ziman, M. & Stoughton, R. Use of hybridization kinetics for differentiating specific from non-specific binding to oligonucleotide microarrays. Nucleic Acids Research 30, e86:1-8 (2002).*
Gao, Y., Wolf, L. K. & Georgiadis, R. M. Secondary structure effects on DNA hybridization kinetics: a solution versus surface comparison. Nucleic Acids Research 34, 3370-3377 (2006).*
Lima, W. F., Monia, B. P., Ecker, D. J. & Freier, S. M. Implication of RNA structure on antisense oligonucleotide hybridization kinetics. Biochemistry 31, 12055-12061 (1992).*
Ratushna, V. G., Weller, J. W. & Gibas, C. J. Secondary structure in the target as a confounding factor in synthetic oligomer microarray design. BMC Genomics 6, 31 (2005).*
Horne, M. T., Fish, D. J. & Benight, A. S. Statistical thermodynamics and kinetics of DNA multiplex hybridization reactions. Biophysical Journal 91, 4133-4153 (2006).*
Susnow, R. G., Dean, A. M., Green, W. H., Peczak, P. & Broadbelt, L. J. Rate-Based Construction of Kinetic Models for Complex Systems. Journal of Physical Chemistry A 101, 3731-3740 (1997).*
Dahlquist, G. & Björck, Å. Numerical Methods. (Dover Publications, 2003). Excerpt of p. 146.*
International Preliminary Report on Patentability for PCT/US2013/045319 dated Dec. 16, 2014.
Wenska, et al., "An activated triple bond linker enables 'click' attachment of peptides to oligonucleotides on solid support," (2011), 39(20):9047-9059.
Biswas et al., "Branch Migration Through DNA Sequence Heterology", J. Mol. Biol. (1998) 279, 795-806.
Braasch et al., "Locked nucleic acid (LNA): fine-tuning the recognition of DNA and RNA", Chemistry & Biology, 8 (2001) 1-7.
Doktycz, "Nucleic Acids: Thermal Stability and Denaturation," Encyclopedia of Life Sciences, pp. 1-18, John Wiley & Sons Ltd, Chichester. http://www.els.net [doi: 10.1038/npg.els.0003123] (Oct. 2002).

(Continued)

*Primary Examiner* — Soren Harward
(74) *Attorney, Agent, or Firm* — Sheppard Mullin Richter & Hampton LLP

(57) ABSTRACT

An approach to designing a polynucleotide probe to hybridize selectively to a target polynucleotide sequence involves calculating the final concentration of the intended binding product between a candidate probe and the target sequence. The calculation takes into consideration the binding reaction between the candidate probe and the target fragment on the target sequence, as well as various other binding reactions, involving either the probe or the target fragment, that interfere with the intended binding reaction. In contrast to the conventional technology, which attempts to determine the entire structure of the target polynucleotide, this approach only needs to determine the binding dynamics that impact on the intended probe-target fragment binding. The approach does not require determination of the structure of the involved sequences.

8 Claims, 12 Drawing Sheets

Specification includes a Sequence Listing.

(56) References Cited

OTHER PUBLICATIONS

Dragulescu-Andrasi et al., "Cell-permeable GPNA with appropriate backbone stereochemistry and spacing binds sequence-specifically to RNA", Chem. Commun., 2005, 244-246.
Dragulescu-Andrasi et al., "A Simple ☐-Backbone Modification Preorganizes Peptide Nucleic Acid into a Helical Structure", J. Am. Chem. Soc. 2006, 128, 10258-10267.
Endy, et al., "Modelling cellular behavior", Nature, vol. 409, pp. 391-395, (2001).
Freier et al., "The ups and downs of nucleic acid duplex stability: structure-stability studies on chemically-modified DNA:RNA duplexes", Nucleic Acids Research, 1997, vol. 25, No. 22, 4429-4443.
Frezza et al., "Modular Multi-Level Circuits from Immobilized DNA-Based Logic Gates", J. Am. Chem. Soc., 2007, 129, pp. 14875-14879.
Hagan, et al., "Mechanisms of kinetic trapping in self-assembly and phase transformation", The Journal of Chemical Physics, 135: 104115-1-104115-13, (2011).
Kahan et al., "Towards molecular computers that operate in a biological environment", Science Direct Physica D 237, (2008) 1165-1172.
Krane et al., "Time for DNA Disclosure", Science, vol. 326, Dec. 18, 2009, 1631-1633.
Kutyavin et al., "Oligonucleotides Containing 2-Aminoadenine and 2-Thiothymine Act as Selectively Binding Complementary Agents", Biochemistry 1996, 35, 11170-11176.
Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," Nucleic Acids Res. 14(22):9081-9093 (1986).
Latimer et al., "Synthetic repeating sequence DNAs containing phosphorothioates: nuclease sensitivity and triplex formation," Nucleic Acids Res. 17(4):1549-1561 (1989).
Lee et al., "Chitosan: a novel platform in proton-driven DNA strand rearrangement actuation", Mol. BioSyst. 2009, 5, 391-396.
Li et al., "A new class of homogeneous nucleic acid probes based on specific displacement hybridization", Nucleic Acids Research, 2002, vol. 30, No. 2, e5, 9 pages.
Lusvarghi, et al., "Loop and backbone modifications of peptide nucleic acid improve G-Quadruplex binding selectivity", JACS, 131, 18415-18424, (2009).
Maugh II, "Wolf & Lamb Chemistry, Many useful reactions difficult to perform by conventional means can be carried out easily with polymeric reagents", Science, vol. 217, Aug. 20, 1982, pp. 719-720.
Nielsen et al., "An Introduction to Peptide Nucleic Acid", Current Issues Molec. Biol. (1999), 1(2): 89-104.
Nishikawa, et al., "DNA computation simulator based on abstract bases", Soft Computing 5: 25-38, (2001).
Ortega et al., "Binding Affinities of Oligonucleotides and PNAs Containing Phenoxazine and G-Clamp Cytosine Analogues Are Unusually Sequence Dependent", Organic Letters, 2007, vol. 9, No. 22, 4503-4506.
Panyutin et al., "Formation of a Single Base Mismatch Impedes Spontaneous DNA Branch Migration", J. Mol. Biol. (1993), 230, 413-424.
Panyutin et al., "The kinetics of spontaneous DNA branch migration", Proc. Natl. Acad. Sci., USA, vol. 91, pp. 2021-2025, Mar. 1994.
Picuri et al., "Universal Translators for Nucleic Acid Diagnosis", J. Am. Chem. Soc. 2009, 131, 9368-9377.
Sager, et al., "Designing nucleotide sequences for computation: A survey of constraints", DNA11, LNCS 3892: 275-289, (2006).
Sahu et al., "Synthesis of Conformationally Preorganized and Cell Permeable Guanidine-Based-Peptide Nucleic Acids (GPNAs)", J. Org. Chem. 2009, 74, 1509-1516.
Seelig et al., "Enzyme-Free Nucleic Acid Logic Circuits", Science, vol. 314, Dec. 8, 2006, pp. 1585-1588.
Sugimoto, et al., "Thermodynamics parameters to predict stability of RNA/DNA hybrid duplexes", Biochemistry, 34: 11211-11216, (1995).
Summerton et al., "Review Article Morpholino Antisense Oligomers: Design, Preparation, and Properties", Antisense and Nucleic Acid Drug Development 7: 187-195 (1997).
Tajima et al., "Direct Oxidative Cyanation Based on the Concept of Site Isolation", J. Am. Chem. Soc. 2008, 130, 10496-10497.
Uhlmann, et al., "Synthesis and properties of PNA/DNA Chimeras", Angew. Chem. Int. Ed. Engl., 35, No. 22, 2632-2635, (1996).
Voelcker et al., "Sequence-Addressable DNA Logic", Small 2008, 4, No. 4, pp. 427-431.
Voit, "Sequential One-Pot Reactions Using the Concept of Site Isolation", Angew. Chem. Int. Ed. 2006, 45, 4238-4240.
Yashin et al., "Networking Particles over Distance Using Oligonucleotide-Based Devices", J. Am. Chem. Soc., 2007, 129, 15581-15584.
Zhang et al., "Control of DNA Strand Displacement Kinetics Using Toehold Exchange", J. Am. Chem. Soc., 2009, 131, 17303-17314.
Zhang et al., "Engineering Entropy-Driven Reactions and Networks Catalyzed by DNA", Science, vol. 318, Nov. 16, 2007, 1121-1125.
Zhou et al., "Novel Binding and Efficient Cellular Uptake of Guanidine-Based Peptides Nucleic Acids (GPNA)", J. Am. Chem. Soc. 2003, 125, 6878-6879.
Koehler, R.T. et al., "Effects of DNA secondary structure on oligonucleotide probe binding efficiency", Computational Biology and Chemistry, vol. 29, No. 6, pp. 393-397 (2005).
Mei, R. et al., "Probe selection ofr high-density oligonucleotide arrays", PNAS, vol. 100, No. 20, pp. 11237-11242 (2003).
PCT/US2013/045319 International Search Report and Written Opinion of the International Searching Authority dated Sep. 16, 2013.

* cited by examiner

SEQUENCE LISTING

```
<160> NUMBER OF SEQ ID NOS: 1

<210> SEQ ID NO 1
<211> LENGTH: 250
<212> TYPE: RNA
<213> ORGANISM: Unknown
<220> FEATURE:
<223> OTHER INFORMATION: Description of Unknown: Target RNA sequence

<400> SEQUENCE: 1
aagacacaca aucgacagag uagggcgccg cgcccaucca cacgagugug uuaagcuaca       60
gacuucaagc cuuaaacuuc guacaucugc aucuugugcg aucuuggcau agcacgggcg     120
ggaccauagg ccccguugga ccaacgaaca aaucuuccuu agguauucga gauugacacc     180
gggcggauca gaucagugcu acuguuugua uauaaacgua aacuaauagu guauugcccg     240
uacacccgac                                                            250
```

POLYNUCLEOTIDE PROBE DESIGN

CROSS-REFERENCE TO RELATED APPLICATIONS

This application claims the benefit under 35 U.S.C. § 119(e) to U.S. provisional application Ser. No. 61/660,145, filed Jun. 15, 2012, the contents of which are incorporated by reference here in its entirety.

SEQUENCE LISTING

The instant application contains a Sequence Listing which has been submitted in ASCII format via EFS-Web and is hereby incorporated by reference in its entirety. The ASCII copy, created on Jun. 21, 2013, is named 097450-0118_SL.txt and is 872 bytes in size.

FIELD OF THE DISCLOSURE

The present disclosure generally relates to methods for designing a polynucleotide probe (e.g., primer, probe, siRNA or antisense) that selectively hybridizes to a target polynucleotide sequence.

BACKGROUND

Relatively short polynucleotide sequences are commonly used to selectively hybridize to a target polynucleotide sequence for various reasons. One such example is polymerase chain reaction (PCR) primers, which are typically designed in pairs to specifically amplify the sequence between them on a target polynucleotide. Like primers, a probe, whether used in real time PCR, in situ hybridization or on microarrays, can be used to identify the presence or concentration of the target sequence. Another example is a small interfering (siRNA), which mediates RNA interference that selectively silences a target gene. For the purpose of this disclosure, a polynucleotide that is designed to selectively hybridize or bind to a target polynucleotide is generically referred to as a "polynucleotide probe" or simply a "probe." In this context, the fragment of the target polynucleotide that actually forms hydrogen bonds with the probe is referred to as the "target fragment."

Various factors contribute to the ability of a probe to selectively and effectively bind a target fragment on a target polynucleotide. For instance, off-target DNA or RNA sequences that bear certain sequence identity to the probe sequence can bind to the probe and thus interfere with the probe's ability to bind the target polynucleotide. Likewise, secondary structure of an RNA molecule that involves binding between the target fragment and another fragment in the RNA molecule will require disruption energy to free the target fragment from such binding in order to make the target fragment accessible for binding to the probe. Determination of the secondary structure of an RNA molecule, however, is difficult.

SUMMARY

Accordingly, the present disclosure provides methodology for evaluating the selectivity and effectiveness of a candidate polynucleotide probe for binding to a target polynucleotide sequence. Accordingly, candidate probes can be compared based on such evaluation providing information for selecting suitable probes. Computer devices and media suitable for carrying out the methodology are described as well.

In accordance with one aspect of the invention, therefore, a method is provided for obtaining information on how effectively a nucleotide probe selectively binds a target fragment in a target nucleotide sequence in a sample, the method comprising: (a) examining the target sequence for fragments capable of binding to the target fragment or the probe; (b) generating equations to represent the binding reaction between the probe and the target fragment and the binding reactions identified in step (a); and (c) solving the equations, for a lapsed time, to determine the concentration of the binding product between the probe and the target fragment, wherein at least one of the steps is performed by a computer.

In one embodiment, the binding reactions identified in step (a) include at least one involving at least part of the target fragment. In another embodiment, the binding reactions identified in step (a) include at least one involving at least part of the probe.

In one embodiment, the at least one binding reaction is intra-strand. In another embodiment, the at least one binding reaction is inter-strand.

In some embodiments, step (a) further comprises examining a plurality of polynucleotides in the sample for fragments capable of binding to the target fragment or the probe.

In some embodiments, the generation of the equations comprises computing equilibrium rates of the bindings. In one aspect, the equilibrium rates are computed with a nearest neighbor algorithm.

In some embodiments, the generation of the equations comprises computing kinetic rates of the bindings.

In some embodiments, the equations are ordinary differential equations or stochastic simulation equations.

In some embodiments, the equations comprise concentrations of one or more of the polynucleotides of the plurality.

In some embodiments, the probe is a primer, a hybridization probe, an siRNA or an antisense polynucleotide. In some embodiments, the sample is a cell.

Computer systems for carrying out the disclosed methods and non-transitory computer-readable medium comprising program code for carrying out such methods are also provided.

BRIEF DESCRIPTION OF THE DRAWINGS

The figures of the accompanying drawings describe provided embodiments by way of illustration and not limitation, in which.

Figure 1:
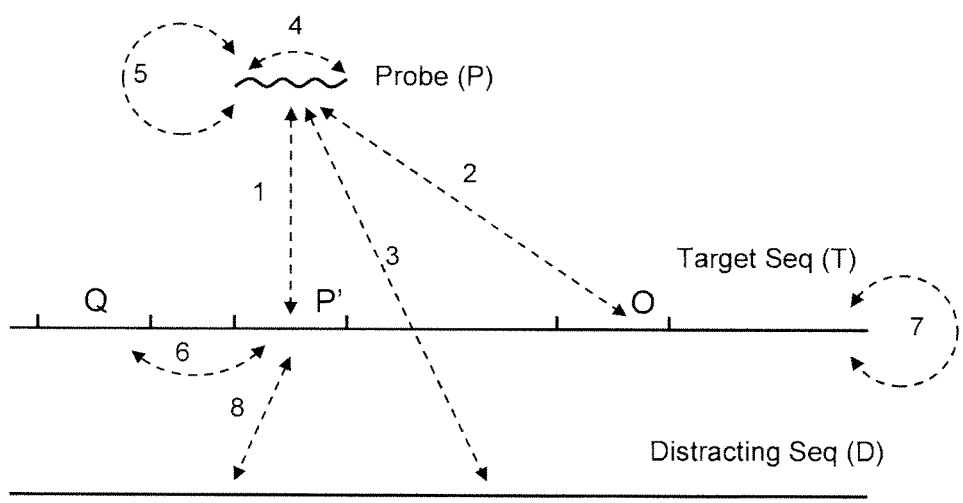
FIG. 1 illustrates various bindings between probe, the target polynucleotide and other polynucleotides as discussed in the disclosure.

It will be recognized that some or all of the figures are schematic representations for exemplification and, hence, that they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION OF THE DISCLOSURE

Certain terms employed in this description have the following defined meanings. Terms that are not defined have their art-recognized meanings.

As used in the specification and claims, the singular form "a", "an" and "the" include plural references unless the context clearly dictates otherwise.

The term "comprising" is intended to mean that the devices and methods include the recited components or steps, but not excluding others. "Consisting essentially of" when used to define devices and methods, shall mean excluding other components or steps that would materially affect the basic and novel characteristics of the technology. "Consisting of" shall mean excluding any components or steps not specified in the claim. Embodiments defined by each of these transition terms are within the scope of this disclosure.

Probe Design

Pursuant this description, an approach is provided for designing a polynucleotide probe that selectively binds a target polynucleotide sequence. The approach avoids "kinetic trapping," a problem inherent with the conventional thermodynamic methods, whereby formation of a given order or structure, even if favored thermodynamically, occurs extremely slowly. See, e.g., Hagen et al., *J. Chem. Physics* 135: 104115 (2011). As a consequence, the described approach affords results that were unachievable heretofore in a practical period of time. Another problem with thermodynamic methods is called the "planar assumption." The planar assumption is a computational simplification that assumes that structures can contain no pairing that cross each other to produce structures known as pseudoknots. The justification for this assumption is primarily computational, which makes the problem easier to solve, since pseudoknots have been found in nature many times. The method of the present disclosure doesn't require making these simplification assumptions and thus considers the formation of pseudoknots as part of its selection criteria.

In related vein, moreover, methodology is provided for assessing the ability of a candidate probe to bind the target sequence selectively and effectively. A suitable probe can be selected on the basis of such assessments.

"Polynucleotide probe" or simply "probe" refers to any polynucleotide that selectively binds (i.e., hybridizes) to a target polynucleotide by virtue of their sequence complementarity. The sequence complementarity need not be perfect, so long as the binding or hybridization can occur under suitable experimental conditions.

In one aspect, a probe is shorter than about 150 nucleotides. In another aspect, a probe is shorter than about 120, 100, 80, 70, 60, 50, 40, 30, 29, 28, 27, 26, 25, 24, 23, 22, 21, 20, 19, 18, 17, 16 or 15 nucleotides. In yet another aspect, a probe is at least about 10 nucleotides long, or alternatively at least about 11, 12, 13, 14, 15, 16, 17, 18, 19, 20, 21, 22, 23, 24, 25, 26, 27, 28, 29, 30, 40, 50, 60, 70, 80, 100, 120, or 150 nucleotides long.

A probe in this regard can be a DNA probe or an RNA probe. Whether DNA or RNA, the probe can be modified chemically or biologically, such as by labeling. The labeling can be, for instance, with radioisotope or fluorescence.

Non-limiting examples of probes include primers, hybridization probes such as those used in in situ hybridization, real-time PCR, or microarray, siRNA, and antisense polynucleotides.

Many factors can be considered when selecting a probe having suitable selectivity and efficiency. Typically, a probe (e.g., siRNA) is shorter than the target polynucleotide (e.g., mRNA) and forms inter-strand hydrogen bonds with a fragment of the target polynucleotide, which is referred to as the "target fragment." One factor to be considered is that the probe should have high or even perfect sequence complementarity with the target fragment on the target polynucleotide. At the same time, the probe should avoid having sequence complementarity with other polynucleotides (off-target polynucleotide) in a sample.

In this context, "off-target polynucleotide" and "distracting polynucleotide" are used synonymously to connote any polynucleotide other than the target polynucleotide in a biological sample. Thus, if the biological sample is a cell or a tissue sample then a distracting polynucleotide is any DNA or RNA molecule in the cell or genome other than the target DNA or RNA.

It is known that the structure (e.g., secondary structure) of a polynucleotide reduce the accessibility of the polynucleotide for binding to be probe. Determination of the structure of the entire polynucleotide, however, is computationally expensive or even infeasible under certain circumstances.

Accordingly, the present disclosure provides in one aspect a methodology for effectively assessing the binding efficiency of a candidate probe to a target polynucleotide. Pursuant to one embodiment, the method calculates the thermodynamics for the intended binding reaction between the candidate probe and the target fragment on the target polynucleotide. In another embodiment, the method further considers binding reactions that can potentially occur in a biological sample, which binding reactions involve either the candidate probe or the target fragment of the probe.

Non-limiting examples of such binding reactions are illustrated in FIG. 1 and annotated in Table 1, as reactions 2-8.

TABLE 1

Binding reactions that can be considered in the assessment

| Reaction No. | Between | | Reaction Order |
|---|---|---|---|
| 1 | Probe (P) | Target fragment (P') on Target sequence (T) | $2^{nd}$ |
| 2 | Probe (P) | An off target site (O) on Target sequence | $2^{nd}$ |
| 3 | Probe (P) | Distracting polynucleotide (D) | $2^{nd}$ |
| 4 | Part of Probe (P) | Another part of Probe (P) | $1^{st}$ |
| 5 | Probe (P) | Another copy of Probe (P) | $2^{nd}$ |
| 6 | Target fragment (P') | Another fragment (Q) on Target sequence (T) | $1^{st}$ |
| 7 | Target fragment (P') | Another copy of Target sequence (T) | $2^{nd}$ |
| 8 | Target fragment (P') | Distracting polynucleotide (D) | $2^{nd}$ |
| 9 | Target fragment (P') | A sequence complementary to P' (A) in A = A' duplex | $2^{nd}$ |
| 10 | Target fragment (P') in P = P' duplex | A sequence complementary to P' (A) in A = A' duplex | $2^{nd}$ |
| 11 | Target fragment (P') | A sequence complementary to P' (A) | $2^{nd}$ |
| 12 | A sequence complementary to P' (A) | A's complementary sequence (A') | $2^{nd}$ |

As shown in FIG. 1 binding reaction 1 is the intended binding between the probe and target fragment. Binding reactions 2-5, on the other hand, are bindings that involve all or part of the probe. Such bindings, therefore, compete with the intended binding by interfering with the probe. Further, binding reactions 6-8 involve the target fragment and thus compete with the intended binding by interfering with the target fragment.

In some embodiments the assessment does not take into consideration bindings that do not involve the probe or the target fragment. For instance, in the scenario of FIG. 2A, where the target fragment (P') can bind to another fragment (A) on the target sequence, the binding reaction (11) between P' and A is taken into consideration for the purpose of the assessment. By contrast, the binding reaction (12) between A and another fragment (A') is not considered. Since reaction 12 effectively distracts A from binding with P', not considering such a reaction in the assessment might lead to underestimation of the effectiveness of a candidate probe. Yet, commonly more than one suitable probes can be identified for a target sequence. Therefore, such underestimation is an acceptable or even favorable consequence, given the greatly improved efficiency of the assessment achieved by not considering such reactions.

When correction of the such underestimation is desired, additional binding reactions can be considered. Given the scenario of FIG. 2A, for instance, if the binding between the target fragment (P') and A is stable but the binding between A and A' is more stable, then not taking the binding between A and A' into consideration can lead to greatly underestimated accessibility of P' by the probe (P); hence, in an underestimation of the efficiency of P. Binding reactions also can be considered, therefore, that involve off-target polynucleotides or off-target fragments on the target nucleotide that potentially can bind the probe or the target fragment. Conversely, while such underestimation allows for false-negative outcomes it ensures that a false-positive outcome is not selected.

Figure 2A:
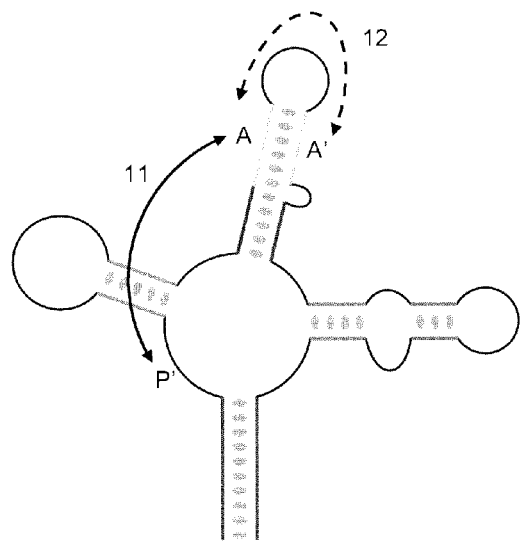
FIG. 2A shows a structure of an exemplary RNA molecule and FIG. 2B illustrates a strand exchange reaction (upper) and a duplex exchange reaction (lower)

In the scenario of FIG. 2A, furthermore, where the binding between A and A' is considered, strand exchange reactions (e.g., "reaction 9" in FIG. 2B, upper panel, reaction 9) and duplex exchange reactions (e.g., "reaction 10" in FIG. 2B, lower panel) can be included to calculate the interaction of these bindings.

The assessment methodology of the present disclosure does not determine the structure (e.g., secondary structure) of the target sequence or the structure of any sequence in the sample. In contrast to conventional technology, which attempts to determine the entire structure of the target polynucleotide, the methodology of the present disclosure only needs to determine the binding dynamics that impact, directly or indirectly, on the intended probe-target fragment binding.

Another unique aspect of the present disclosure, as will be described below, is that, in some embodiments, the subject assessment methodology takes into consideration concentrations or copy numbers of the distracting polynucleotide sequences in a biological sample. In this context, it is noted that polynucleotides that are highly concentrated in a sample, such as an rRNA, can cause more interference to the intended binding than those with low copy numbers.

Sequence Analysis Procedure

In one aspect, the present disclosure provides methods for assessing the selectivity and/or effectiveness of a candidate probe in binding a target polynucleotide. Then comparison can be made among a number of candidate probes, thereby to determine the best one or ones for further experimental testing. The following sections, along with FIG. 3, illustrate a sequence analysis procedure (100) for such an assessment.

A. Identification of Potential Binding Reactions

Figure 3:
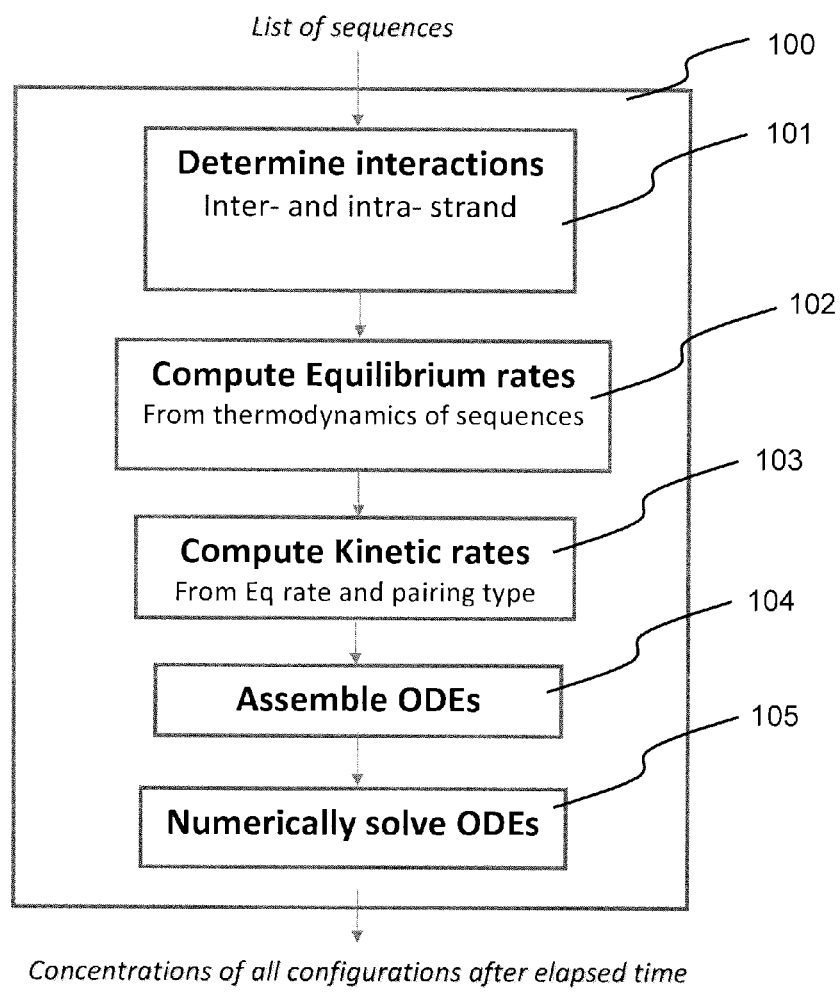
FIG. 3 lists exemplary steps for evaluating a candidate probe sequence.

In accordance with one embodiment, the method starts with identifying potential binding reactions in a biological sample that involve the candidate probe or the target fragment (see FIG. 3, step 101). Such reactions can be identified via known techniques, such as sequence alignment between the selected target fragment (or the probe) and the genomic sequence of the cell.

In this regard certain thresholds can be used for determining whether a reaction can occur. For instance, any alignment with less than a certain percentage of sequence identity (e.g., 70%, 75%, 80%, 85% or 90%) or fewer than a certain number of identical nucleotides (e.g., 2, 3, 4, 5, 6, 7 8, 9, or 10) can be ruled out. In some aspects, the thresholds do not need to be high because the actual binding reactions can be simulated or calculated via steps described below.

Sequence alignment can be used to determine complementary regions for potential binding reactions. Binding reactions that actually occur may be more limited, however.

Figure 4:
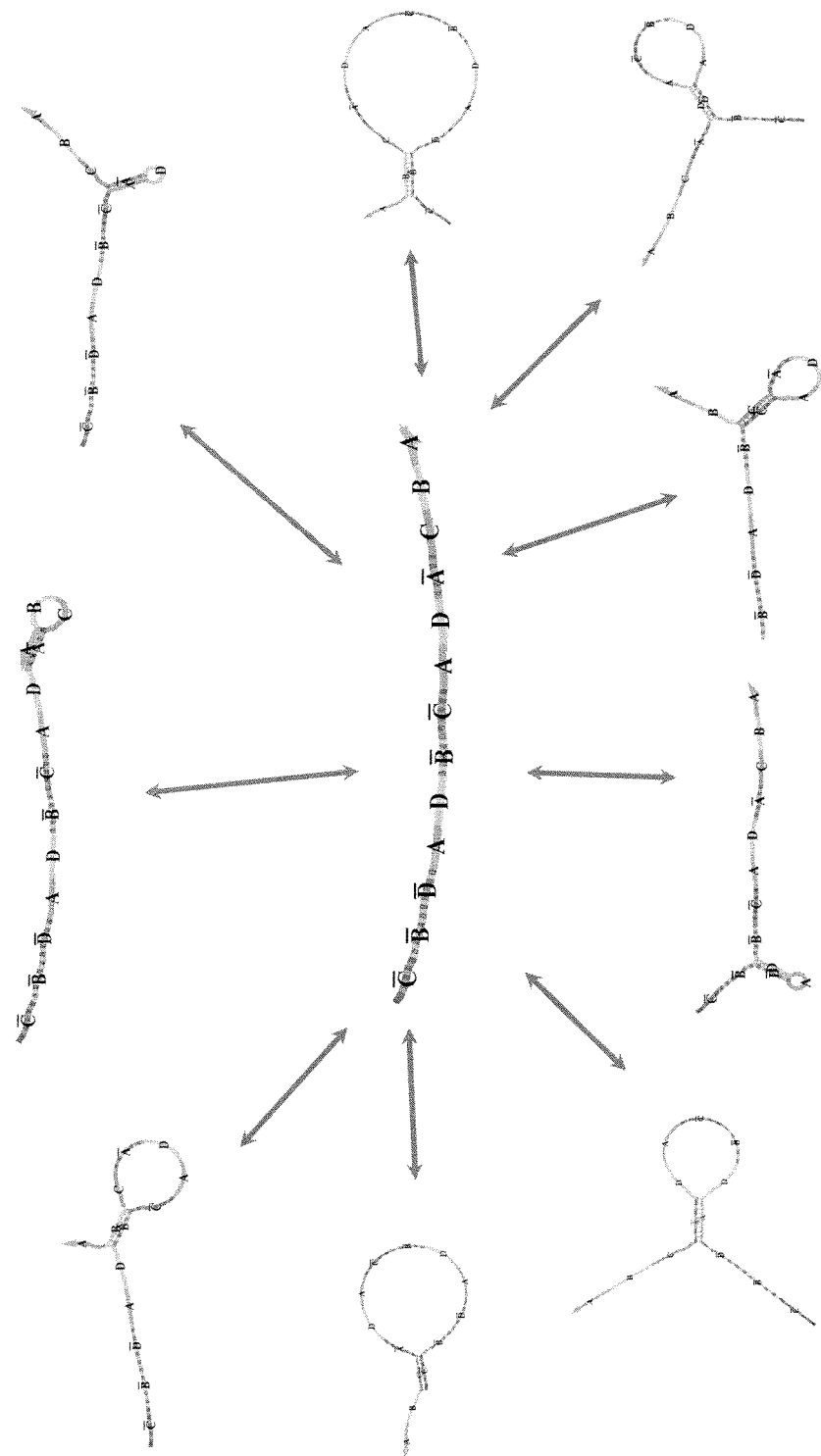
FIG. 4 illustrates a method to determine potential binding reactions involving fragments of a polynucleotide strand, assuming that once a strand is involved in a reaction, the resulting product does not participate in further reactions.
Figure 5:
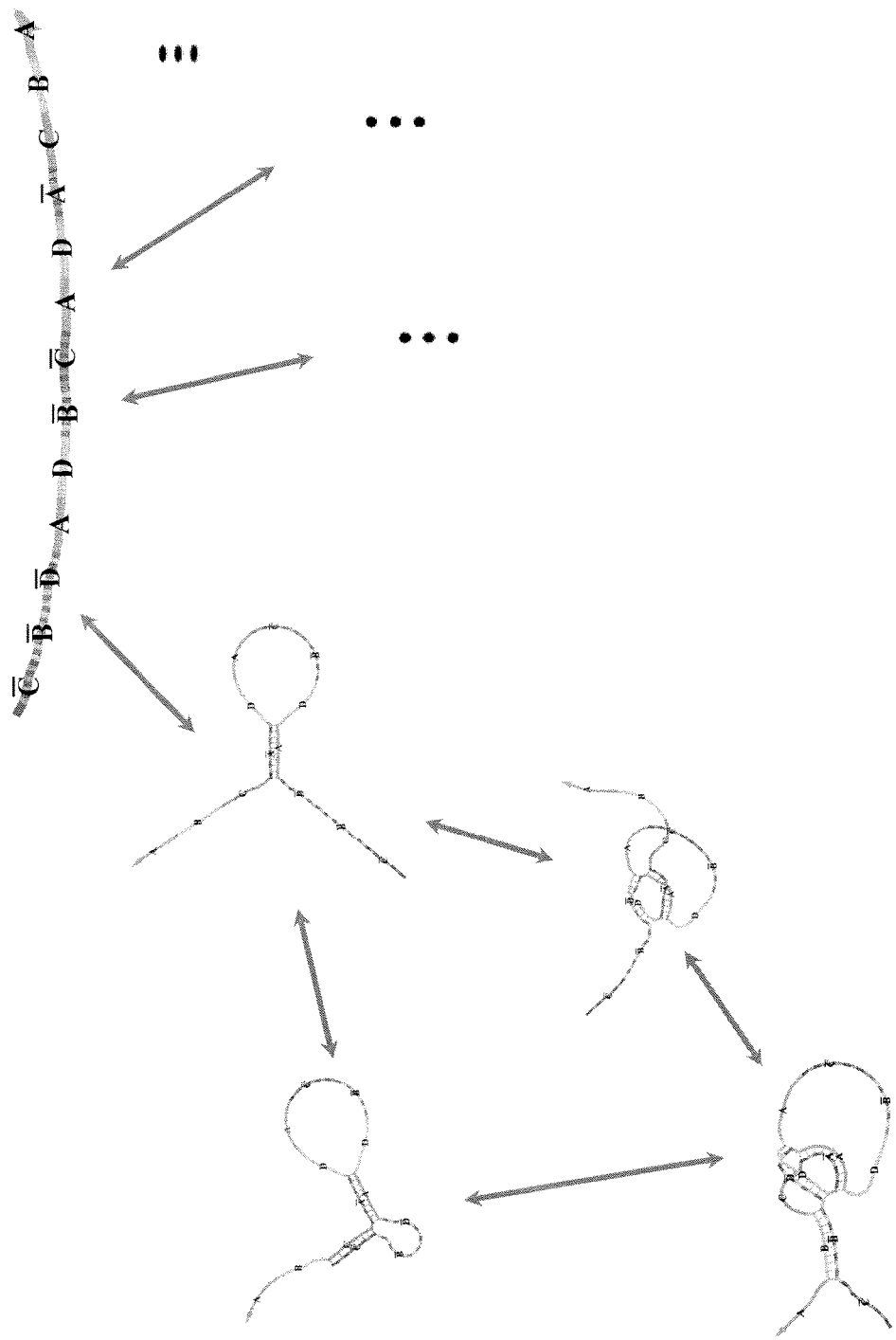
FIG. 5 illustrates a method to determine potential binding reactions involving fragments of a polynucleotide strand, in which the strand, after being involved in a reaction, is allowed to participate in new reactions.

Consider the example depicted in FIG. 4, which assumes that a fragment, once it participates in a binding reaction, cannot simultaneously bind another fragment. In this example, once a polynucleotide strand is involved in a reaction, the resulting product does not participate in further reactions. In another scenario, illustrated in FIG. 5, a strand is allowed, after involvement in a reaction, to participate in new reactions. The scenario in FIG. 5 contemplates that pruning can be used to avoid consideration of unlikely binding reactions that, for instance, are thermodynamically prohibitive due to spatial constraints. (In FIG. 4 and FIG. 5, a letter with a bar on the top (e.g., $\overline{A}$, $\overline{B}$, $\overline{C}$ or $\overline{D}$) indicates a sequence fragment having complementary sequence to a fragment with a corresponding letter without the bar, e.g., A, B, C or D.)

Figure 2B:
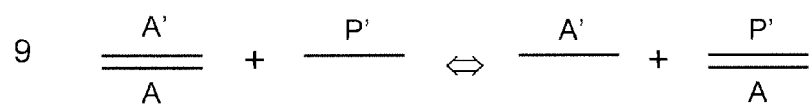
Figure 2B:
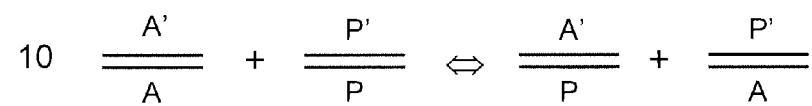

Without limitation, in some embodiments the binding reactions considered in the sequence analysis include one or more of those listed in FIGS. 1, 2A and 2B and Table 1.

As described above, the binding reaction can be intra- or inter-strand (or intra- or inter-polynucleotide). An intra-strand reaction occurs between fragments of a single strand, and an inter-strand reaction occurs between different polynucleotides or different strands. As Table 1 notes, intra-strand reactions (reactions 4 and 6) are first order reactions and inter-strand reactions (reactions 1-3, 5, 7 and 8) are second order reactions. Likewise, reactions 11 and 12 are first order reactions. Further, the orders of reactions 9 and 10 depend on whether the fragments are on the same strand or different strands.

Not all reactions need to be considered in a particular sequence analysis. In one embodiment, for instance, the sequence analysis includes reaction 1 and another reaction of the list. In another embodiment, the sequence analysis includes reaction 1 and two or more, or three or more, or four or more, or five or more, or six or more other reactions of the list. In yet another embodiment, the sequence analysis includes all reactions 1-8. In some embodiments, the sequence analysis includes at least a list of reactions as provided in any row of Table 2.

TABLE 2

Exemplary lists of reactions considered in sequence analysis

| List No. | Reactions |
|---|---|
| 1 | 1, 3 |
| 2 | 1, 2, 3 |
| 3 | 1, 2, 3, 8 |
| 4 | 1, 3, 6, 8 |
| 5 | 1, 3, 6, 8, 9, 11, 12 |
| 6 | 1-8 |
| 7 | 1-12 |

In other embodiments, the sequence analysis leaves unconsidered potential reactions that do not directly involve the probe or the target fragment on the target sequence.

B. Computation of Equilibrium Rates for the Interactions

In some embodiments the equilibrium rate for each binding reaction is calculated (see FIG. 3, step 102) using thermodynamics of involved sequences. A key parameter of this nucleic-acid thermodynamics, the Gibbs free energy ($\Delta G$), can be estimated via a nearest neighbor technique. For more details on this technique, see Santalucia, *Proc. Natl. Acad. Sci. USA* 95: 1460-5 (1998).

More specifically, the interaction between bases on different strands depends to certain extent on the neighboring bases. Accordingly, instead of treating a nucleic acid helix as a string of interactions between base pairs, the nearest-neighbor model treats a nucleic acid helix as a string of overlapping interactions between neighboring base pairs. The nearest neighbor model for nucleic acids assumes that the stability of a given base pair depends on the identity and orientation of neighboring base pairs.

The thermodynamics of binding sequences determines how stable the binding is or, in other words, how much energy ($\Delta G$) is required to break the binding apart. Only the sequences are needed at this step, therefore, in addition to certain constants such as temperature and salt concentrations in the buffer.

C. Computation of Kinetic Rates

The sequence analysis also can include computing the kinetic rates of potential binding reactions. This computation takes as inputs the equilibrium rates and binding types, i.e., intra- or inter-strand binding.

For instance, for the intended reaction 1, a second order reaction,

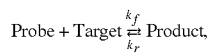

Probe + Target $\underset{k_r}{\overset{k_f}{\rightleftharpoons}}$ Product, can be solved to obtain the forward ($k_f$) and reverse ($k_r$) kinetic rates, provided that $k_{eq}$ is known:

$$k_{eq} = \frac{k_f}{k_r}.$$

In this context, $k_{eq}$ (detailed balance) can be calculated from $\Delta G = -RT \ln(k_{eq})$, where R is the ideal gas law constant and T is the kelvin temperature of the reaction. As described above, $\Delta G$ can be determined from knowledge of the sequences, using a nearest neighbor method or comparable approach.

For a first order reaction, e.g., reaction 5:

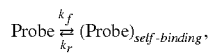

Probe $\underset{k_r}{\overset{k_f}{\rightleftharpoons}}$ (Probe)$_{self-binding}$, the kinetic rates can be determined likewise. Here, $k_f=1$.

For a strand exchange reaction, e.g., reaction 9:

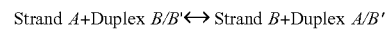

Strand $A$+Duplex $B/B'$ $\leftrightarrow$ Strand $B$+Duplex $A/B'$ or a duplex exchange reaction, e.g., reaction 10:

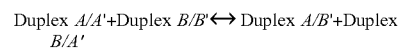

Duplex $A/A'$+Duplex $B/B'$ $\leftrightarrow$ Duplex $A/B'$+Duplex $B/A'$ rates can be parameterized by the length of matching nucleotides, see, e.g., Zhang and Winfree, *J. Am. Chem. Soc.* 131: 17303-14 (2009), even though the nearest neighbor models can also be used.

D. Representation of the Binding Reactions as Ordinary Differential Equations (ODE)

With the kinetic rates calculated for each of the binding reactions, each reaction can be represented as an ordinary differential equation or ODE, e.g., first-order ODE (see FIG. 3, step 104). An ODE is an equation in which there is only one independent variable and one or more derivatives of a dependent variable with respect to the independent variable, whereby all the derivatives occurring in the equation are ordinary derivatives. That the use of ODE to simulate biochemical reactions is well-known is evidenced, for example, by Chen et al., Genes & Development 24: 1861-75 (2010), and H. Metiu, PHYSICAL CHEMISTRY: KINETICS (Taylor & Francis, 2006).

For instance, the following ODE and boundary conditions can be used to describe this reaction:

$$A + B \xrightarrow{k_f} C,$$

$$\frac{dH}{dt} = -k_f * A_t * B_t$$

and $$H_0 = 0,$$

$$A_t = A_0 - H_t,$$

$$B_t = B_0 - H_t,$$

and $$C_t = C_0 + H_t$$

which has the analytical solution:

$$H_t = \frac{A_0 B_0 \left(e^{A_0 k_j} - e^{B_0 k_f}\right)}{A_0 e^{A_0 k_f} - B_0 e^{B_0 k_f}}.$$

Similar solutions apply to $B_t$ and $C_t$.

In addition to ODEs, stochastic simulation equations can also be used. For example, see Endy and Brent, Nature 409: 391-95 (2001).

E. Solving the ODE to Determine the Final Concentration of the Binding Products

At this step (see FIG. 3, step 105), the ODEs are solved for a given elapsed time. The ODEs take initial concentrations of the polynucleotides in the sample as parameters. In one embodiment, analytical solutions are obtained to the ODEs, e.g., by rearranging the calculation and determining the integral. In another embodiment, numeric solutions are obtained.

The elapsed time can be determined with computational simulations. In general, the elapsed time should be long enough to allow the reaction to reach equilibrium or close to it. On the other hand, the elapsed time can be short to minimize the computation burden. Balancing these considerations, one may employ an elapsed time of about 60 seconds. Alternatively, the elapsed time can be at least about 1 second or at least about 2, 3, 4, 5, 10, 20, 30, 40, 50, or 60 seconds, or 2, 3, 4, 5, 10, 20, 30, 40, 50, or 60 minutes, or 1.5, 2, 3, 4, 5, 6, 9, or 12 hours. In another aspect, the elapsed time is not longer than about 12 hours, or 9, 6, 5, 4, 3, 2, or 1.5 hours, 60 minutes or, alternatively, no longer than about 50, 40, 30, 20, 10, 5, 4, 3, or 2 minutes, or no longer than about 60, 50, 40, 30, 20, 10, 5, 4, 3, or 2 seconds. The simulations can be run at several time scales to estimate when the reactions start to level out. Given the exponential scale of rate constants involved, the jump in time frames between meaningful activity goes up more quickly at higher scales.

Concentrations of polynucleotides in a sample may be known or can be estimated. In some embodiments, the sample includes all polynucleotides, whether DNA or RNA, from one or more cells. For DNA fragments, the concentration is similar across the board except for certain highly repeated units. For RNA, the concentrations of each molecule can be, for instance, estimated from existing databases or collected by conducting experiments, e.g., using microarrays. With respect to RNA molecules, in one embodiment all mRNAs are assumed to have the same concentration, whereas the concentrations of tRNA and rRNA can be significantly higher.

Concentrations of polynucleotides in a sample, in some embodiments, are provided as a database of cellular RNA in a cell and their corresponding concentrations in the cell. Such a cell can be a mammalian or human cell which can be targeted by a microorganism. Such a database can be prepared with information readily available in the art. For instance, gene annotations and sequences from several different sequencing databases can be retrieved and combined: UCSC Genome Browser (genome.ucsc.edu), Ensembl (uswest.ensembl.org), NCBI Refseq (ncbi.nlm.nih.gov/refseq), NCBI's CCDS database (ncbi.nlm.nih.gov/CCDS), NCBI Genebank (ncbi.nlm.nih.gov/genbank) and Uniprot's coding sequences (uniprot.org). Both known and predicted coding sequences, such as ribosomal RNAs, the 45S ribosomal DNA repeating unit, repetitive elements, repeat maskers, microRNAs and tRNAs, can be included in the database.

The different transcripts can then be consolidated with the names to form a single annotated transcript. Approximate or relative concentrations can be given to each category or RNA for the purposes of the kinetic simulations. For instance, the ribosomal RNA can be assumed to be most abundant, and mRNAs are present at relatively low concentrations. These ensemble average numbers can work for the rankings as they can be in the roughly accurate qualitative order or orders to properly penalize probes which bind to, or have their target sites bound to, cellular RNA. Any inaccuracy in these parameters can have bearing on the absolute value of expected proper bound probe concentration at a given incubation time but should impact each simulation proportionally leaving the relative ranking of one probe site vs. another in good order.

Upon solving related ODE for a given elapsed time, the final concentration is determined for the intended binding product. Thus, the final concentration reflects the efficiency of the probe binding to the target sequence. Accordingly, such final concentrations serve as a basis for comparing the efficiencies of different candidate probes for a target polynucleotide. In this context, those that produce the highest concentrations of intended binding products are the most efficient probes.

Computer Systems and Network

The methodology described here can be implemented on a computer system or network. A suitable computer system can include at least a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by but are not limited to central processing units, microprocessors, graphics processing units, physics processing units, digital signal processors, network processors, front end processors, coprocessors, data processors and audio processors. The term "memory" connotes an electrical device that stores data for retrieval. In one aspect, therefore, a suitable memory is a computer unit that preserves data and assists computation. More generally, suitable methods and devices for providing the requisite network data transmission are known.

Also contemplated is a non-transitory computer readable medium that includes executable code for carrying out the described methodology. In certain embodiments, the medium further contains data or databases needed for such methodology.

Embodiments can include program products comprising non-transitory machine-readable storage media for carrying or having machine-executable instructions or data structures stored thereon. Such machine-readable media may be any available media that may be accessed by a general purpose or special purpose computer or other machine with a processor. By way of example, such machine-readable storage media may comprise RAM, ROM, EPROM, EEPROM, CD-ROM or other optical disk storage, magnetic disk storage or other magnetic storage devices, or any other medium which may be used to store desired program code in the form of machine-executable instructions or data structures and which may be accessed by a general purpose or special purpose computer or other machine with a processor. Combinations of the above also come within the scope of "machine-readable media." Machine-executable instructions comprise, for example, instructions and data that cause a general purpose computer, special-purpose computer or special-purpose processing machine(s) to perform a certain function or group of functions.

Embodiments of the present invention have been described in the general context of method steps which may be implemented in one embodiment by a program product including machine-executable instructions, such as program code, for example in the form of program modules executed by machines in networked environments. Generally, program modules include routines, programs, logics, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments of the present invention may be practiced in a networked environment using logical connections to one or more remote computers having processors. Those skilled in the art will appreciate that such network computing environments may encompass many types of computers, including personal computers, hand-held devices, multi-processor systems, microprocessor-based or programmable consumer electronics, network PCs, minicomputers, mainframe computers, and so on. Embodiments of the invention also may be practiced in distributed and cloud computing environments where tasks are performed by local and remote processing devices that are linked, by hardwired links, by wireless links or by a combination of hardwired or wireless links, through a communications network. In a distributed computing environment, program modules may be located in both local and remote memory storage devices.

EXAMPLE

The present disclosure is further illustrated by reference to this example, which demonstrates the performance of the presently described probe design method with a RNA target that is 250 nucleotides (nt) in length (sequence shown in Table 3).

TABLE 3

Nucleic acid sequence (SEQ ID NO: 1) of target RNA sequence for probe design

AAGACACACAAUCGACAGAGUAGGGCGCCGCGCCCAUCCACACGAGUGU

GUUAAGCUACAGACUUCAAGCCUUAAACUUCGUACAUCUGCAUCUUGUG

CGAUCUUGGCAUAGCACGGGCGGGACCAUAGGCCCCGUUGGACCAACGA

ACAAAUCUUCCUUAGGUAUUCGAGAUUGACACCGGGCGGAUCAGAUCAG

UGCUACUGUUUGUAUAUAAACGUAAACUAAUAGUGUAUUGCCCGUACAC

CCGAC

Mathematica® scripts were prepared that examined the target RNA sequence for each potential probe binding site for its ability to bind to probes as well as their possible bindings with other nucleic acid or nucleic acid fragment in a system. As described above, equations were then generated for each potential binding and solved, for a lapsed time, to determine the concentration of binding product. The performance of these potential sites and probes are then ranked based on the determined concentrations of the binding products.

In a first experiment (see ranking results in FIG. 6A), the ranking was run at 60 degrees Celsius with 5 nM target concentrations and 100 nM probe concentrations for all possible 15-nt probes sites along the target RNA target. Kinetic mechanisms were generated automatically, which allowed both the target sequence and the probe sequence to fold in any vicinity that overlaps with the probe binding area, as well as allow the probe to hybridize to any possible partial or full match site along the target. Rate constants were derived from the nearest neighbor free energy of binding, see Sugimoto et al., *Biochemistry* 34: 11211-16 (1995), using the standard forward rate constant for hybridization ($10^5$ per molar per second) and the detailed balance to derive the backwards rate constant. Given this model, the ODEs were solved to determine the concentration of correctly bound probe at a user specified time into the reaction (starting as initially unbound).

A second experiment (see ranking results in FIG. 6B) was conducted similarly to the first experiment, except with the addition of interaction with cellular RNA. To this end, 300 RNA molecules from a cellular RNA database were used. The cellular RNA database was constructed using the method as described above. This adds to the mechanism the ability of any cellular RNA to bind either the probe or any site in the target that overlaps with the probe binding site.

Figure 6A:
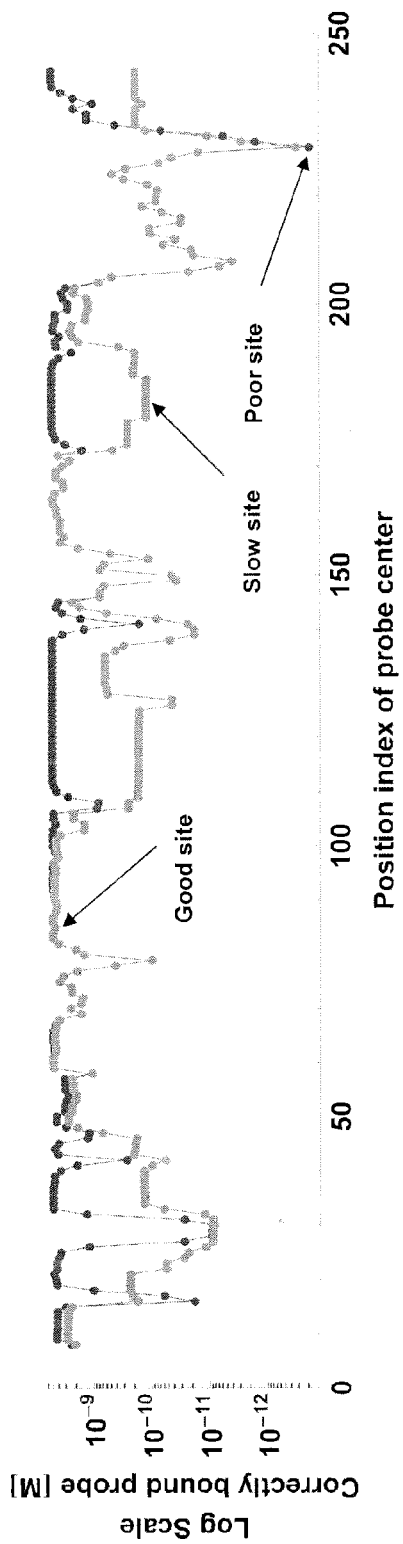
FIG. 6A-B show the ranking results of sites for probes on a target RNA that is 250 nucleotides long.

FIG. 6A shows the comparison, in the first experiment, of systems ranked where the reaction time was limited to 1 hour (shown as connected gray dots) vs. systems ranked where the reactions are permitted to proceed for 1 year (i.e., approximating thermodynamic equilibrium, shown as connected black dots). The traces of log scale concentration of properly bound probe to target site vs. position along the RNA sequence demonstrate that limiting the reaction time to one hour allows one to properly penalize rankings of sequences that may lead to high yield thermodynamically, but will take a very long time to reach equilibrium (i.e., kinetically trapped). The example simulated the most accessible site's time course for one hour, which predicts that 98.916% of the target binding site would end up occupied by the probe after one hour.

Figure 7:
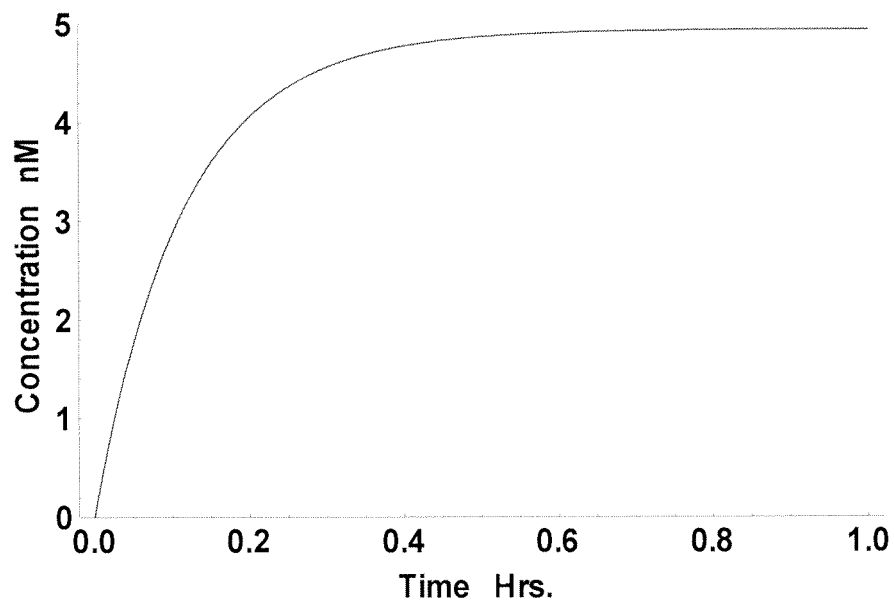
FIG. 7 presents the yield curve of a potential probe binding to a good site.
Figure 8:
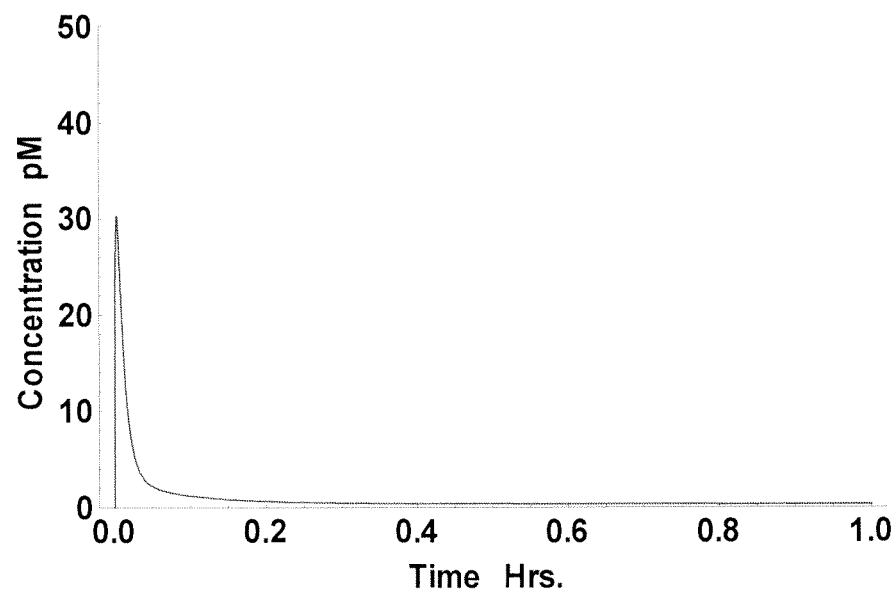
FIG. 8 presents the yield curve of a potential probe binding to a poor site.

FIG. 7 and FIG. 8 demonstrate that the algorithm can correctly identify sites that are thermodynamically inaccessible, which reached less than 0.01% occupancy after one hour. In FIG. 7, the concentration of a "good" site/probe (nt 79-93, as indicated in FIG. 6A) bound to the RNA target rose rapidly within minutes. This probe was ranked high on both curves. A "poor" site/probe (nt 222-236, as indicated in FIG. 6A), which was ranked low on both curves, reached less than 0.01% occupancy after one hour (FIG. 8).

Figure 9:
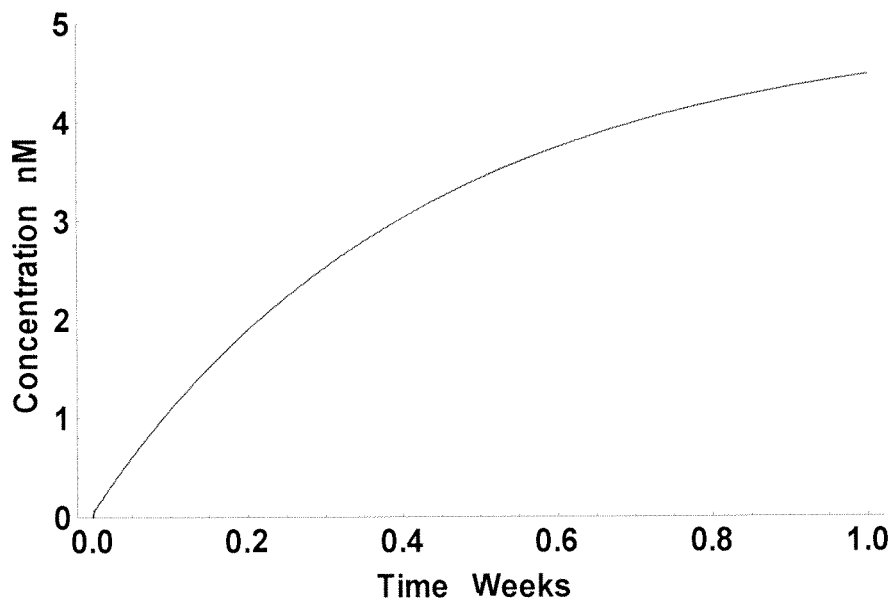
FIG. 9-10 present the yield curves of a potential probe binding to a slow site at different time scales.
Figure 10:
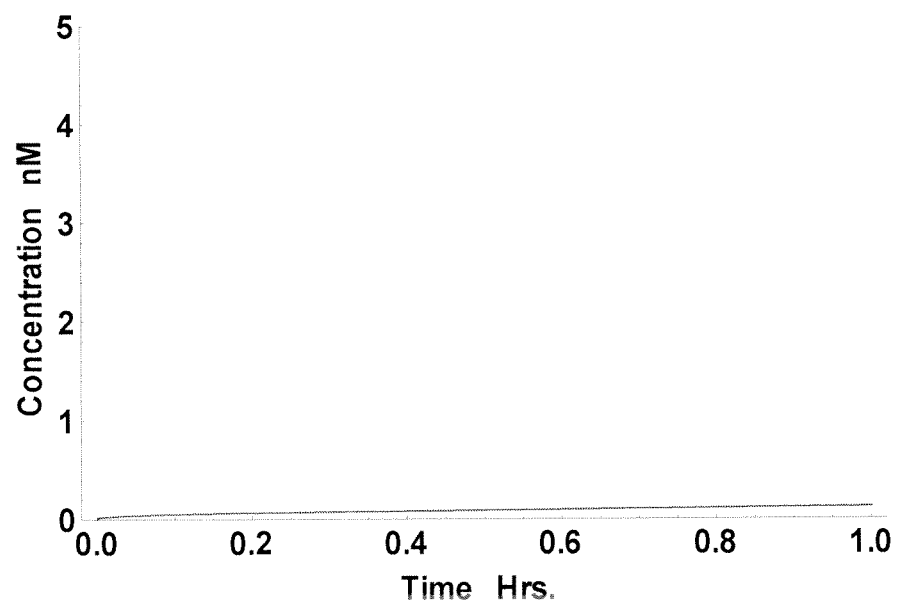
Figure 11:
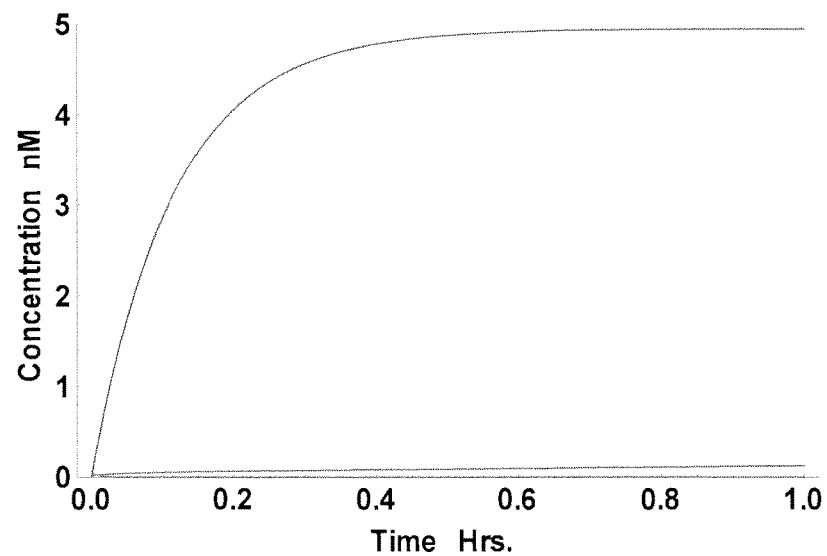
FIG. 11-12 present the yield curves of potential probes binding to a good site (black curves), a slow site (gray curves) and poor site (not visible)
Figure 12:
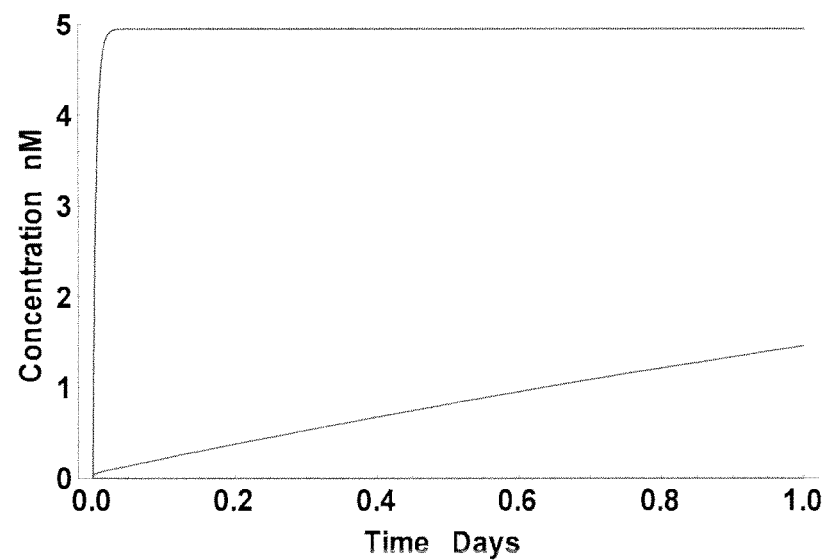

FIG. 9 and FIG. 10 show the performance of a "slow" site/probe (nt 176-190, as indicated in FIG. 6A) that was ranked high on the 1-year curve but relative low on the 1-day curve. This probe was able to reach over 89% year after a week (FIG. 9), abut the yield after an hour was only 2.4% (FIG. 10). Accordingly, the results demonstrate that present technology can identify sequences correctly that, although their equilibrium state may thermodynamically favor high yield, actually behave poorly kinetically. FIG. 11 and FIG. 12 collectively show the comparison of the performance of these three probes (black curve: good site; gray curve: slow site: poor site: not visible), over an hour (FIG. 11) and a day (FIG. 12), respectively.

The second experiment examined the impact on the model of including the presence of cellular RNA. As demonstrated by a plot of concentration of correctly bound probe vs. position index, the presence of cellular RNA penalizes many of the possible sites along the RNA, either by the cellular RNA binding to these sites on the target or by the cellular RNA binding to the probe. This experiment then examined a particular case where a probe in isolation with the target would demonstrate good yield after 1 hour (>87%) but where, when cellular RNA also was considered in the system, yield after one hour drops to only ~40%, and actually takes closer to 5 hours to reach the yield expected from the system in isolation.

Figure 6B:
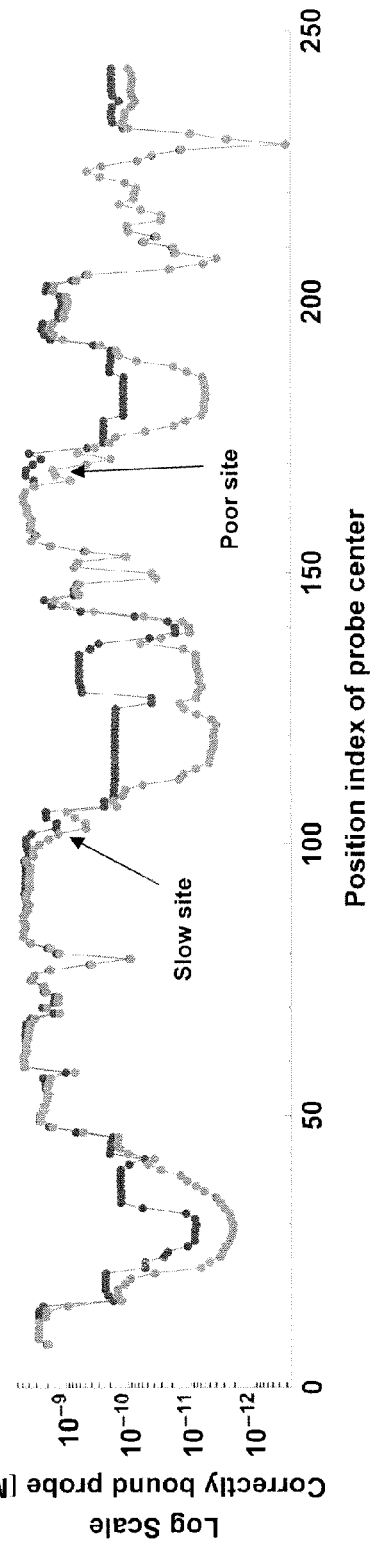
Figure 13:
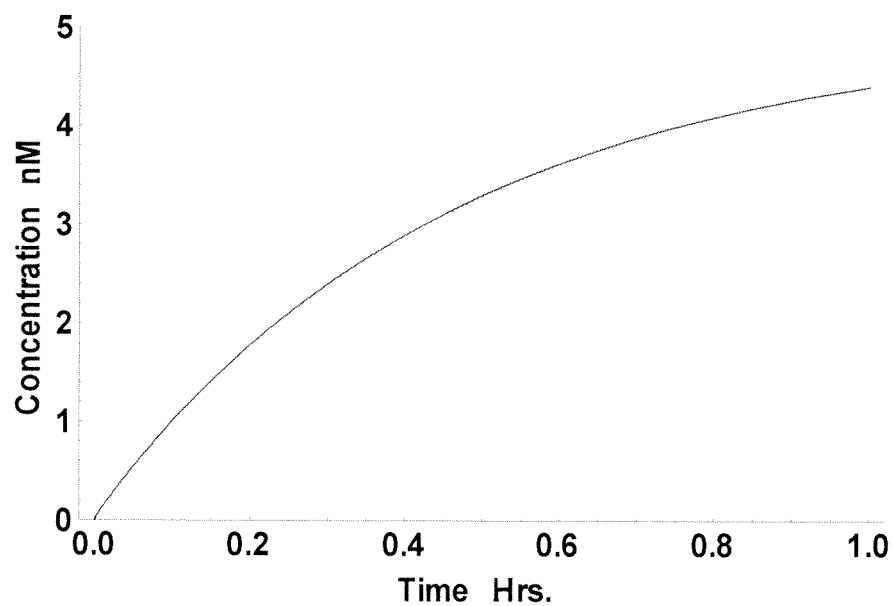
FIG. 13 presents the yield curve of a potential probe binding to a "good" site if not considering the distraction of cellular RNA.
Figure 14:
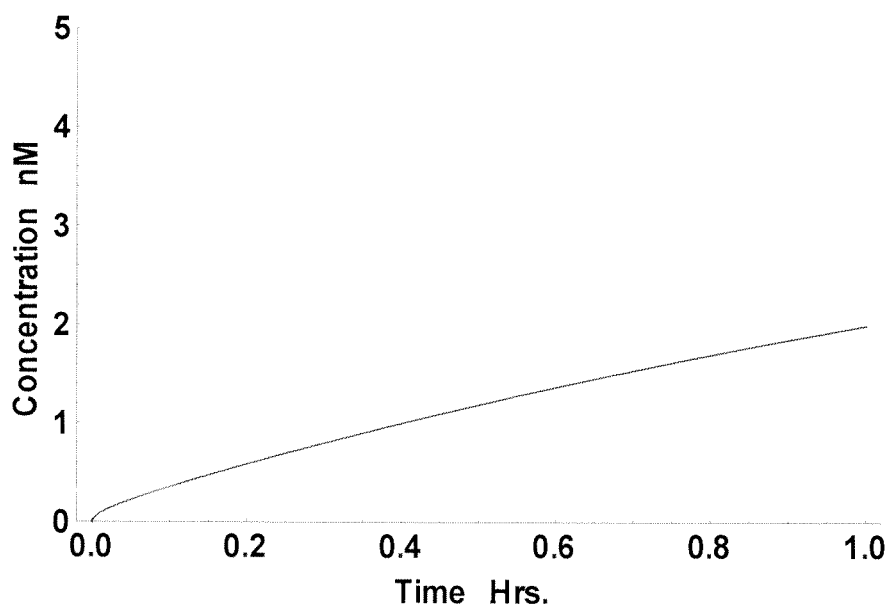
FIG. 14-15 show the reduced performance of the site in FIG. 13 in the presence of cellular RNA. Accordingly, this site is considered a "slow" site in the presence of cellular RNA.
Figure 15:
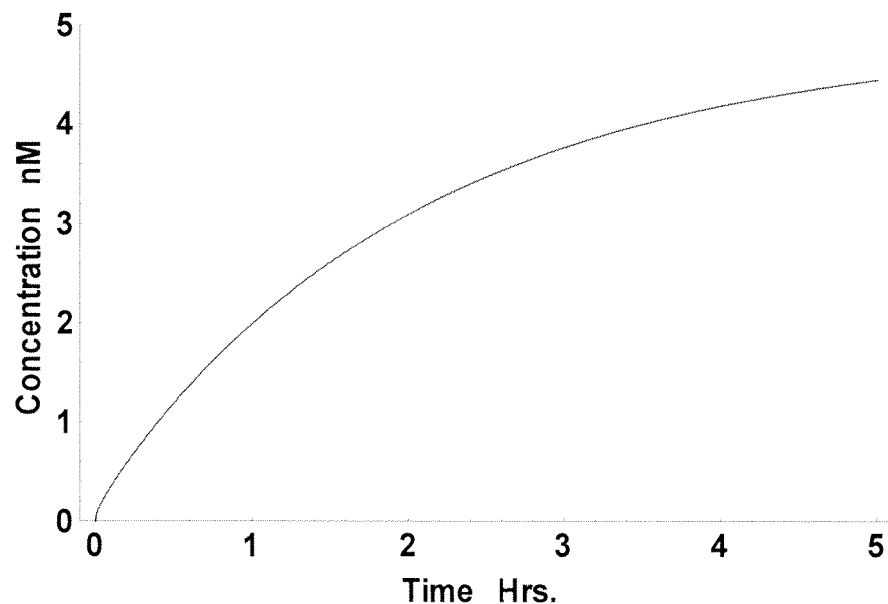

FIG. 6B shows two ranking curves. The black dots indicate the calculated performance of potential probes incubated with the RNA target only, without cellular RNA. The gray dots indicate the calculated performance of potential probes in the presence of cellular RNA. It was observed that ideal sites for probes, without the consideration of distraction from cellular RNA, did not perform as well in the presence of cellular RNA. For instance, FIG. 13 shows the performance of such a "good" site/probe (nt 94-108, indicated as "slow site" in FIG. 6B) in the absence of cellular RNA. By contrast, this probe performed much worse in the presence of cellular RNA (see FIG. 14), taking 5 hours (FIG. 15) to reach a concentration that it would have reached without the distraction of the cellular RNA.

Figure 16:
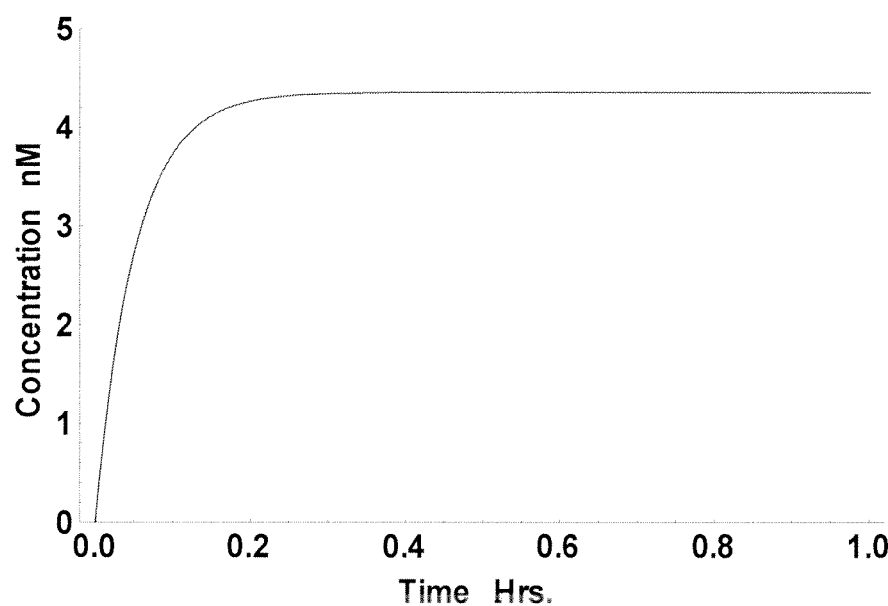
FIG. 16 presents the yield curve of a potential probe binding to a "good" site if not considering the distraction of cellular RNA.
Figure 17:
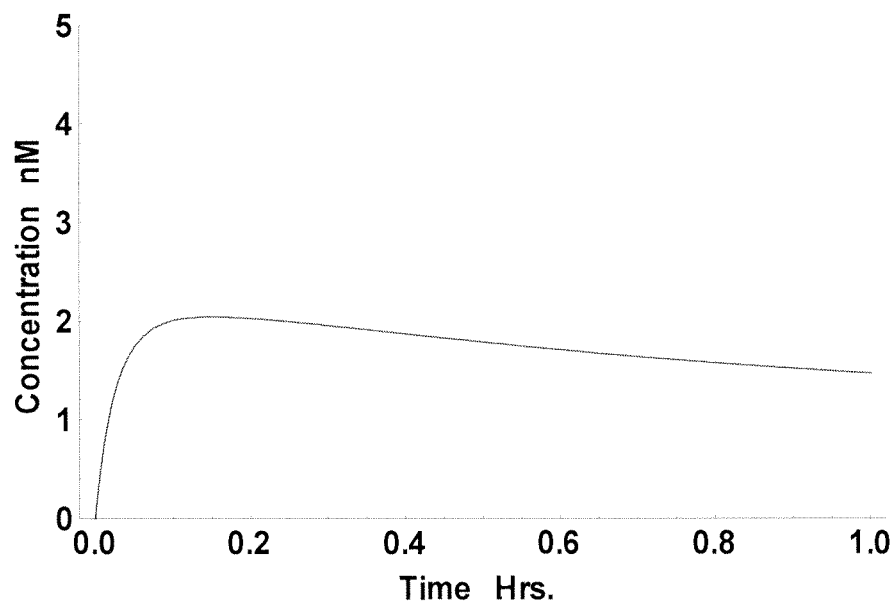
FIG. 17-18 show the reduced performance of the site in FIG. 16 in the presence of cellular RNA. Accordingly, this site is considered a "poor" site in the presence of cellular RNA.
Figure 18:
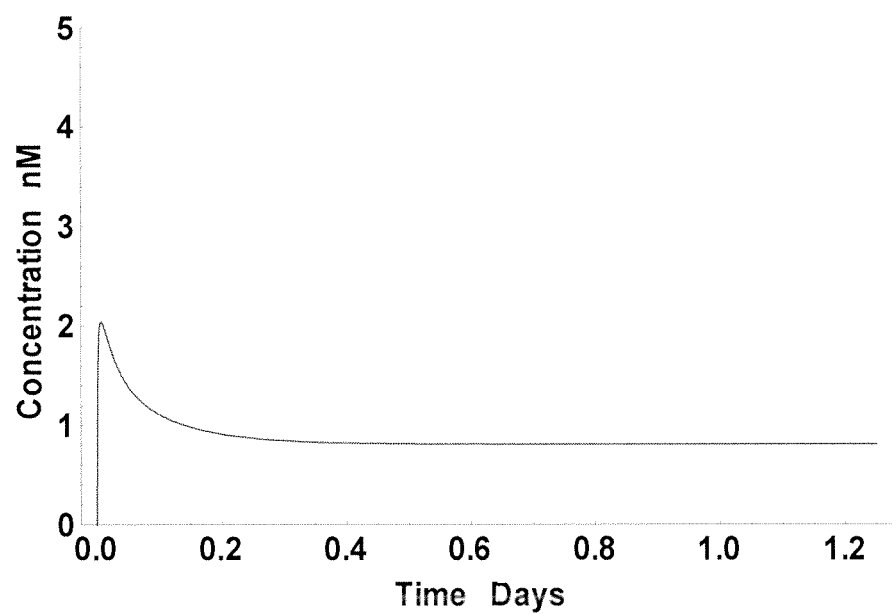

A similar but more dramatic finding was observed with a "poor" site (nt 161-175, as indicated in FIG. 6B). FIGS. 16-18 show that this site performed well in the absence of cellular RNA (FIG. 16) but, in the presence of cellular RNA, could only reach 29% yield after 1 hour (FIG. 17) and, even worse, only 15% yield after 1.2 days (FIG. 18).

Together these results demonstrate how the method of the present disclosure adds subsequent layers of mechanistic complexity, including folding of the probe, folding in and around the target site, mispairing of the probe to the target strand (at unintended binding site), interactions of the probe with cellular RNA, interactions of the target site with cellular RNA, and time limited reactivity to account for kinetic trapping. At each level the algorithm makes the worst-case assumptions regarding binding, penalizing the ranking but not rewarding the binding of the probe to its target site with each layer.

As illustrated, the method uses these worst case assumption-simplified kinetic models, with empirically derived rate constants. Also, the method kinetically solves the system to return ranking scores in units of real world minimum expected concentration of target site to be occupied by the probe sequence candidate. In advance of synthesizing and testing empirically, therefore, the algorithm presents the best possible probe candidates based on the worst-case percentage occupancy that one could expect for any given probe candidate, given only knowledge about the nucleic acid sequences that reside in the cell.

Although the discussions above may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present invention. Such variations will depend on the software and hardware systems chosen and on designer choice. It is understood that all such variations are within the scope of the invention. Likewise, software and web implementations of the present invention could be accomplished with standard programming techniques with rule based logic and other logic to accomplish the various database searching steps, correlation steps, comparison steps and decision steps.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed here. For example, the terms "comprising", "including," containing," etc. shall be read expansively and without limitation. Additionally, the terms and expressions employed here have been used as terms of description and not of limitation; hence, the use of such terms and expressions does not evidence and intention to exclude any equivalents of the features shown and described or of portions thereof. Rather, it is recognized that various modifications are possible within the scope of the invention claimed.

By the same token, while the present invention has been specifically disclosed by preferred embodiments and optional features, the knowledgeable reader will apprehend modification, improvement and variation of the subject matter embodied here. These modifications, improvements and variations are considered within the scope of the invention.

The invention has been described broadly and generically here. Each of the narrower species and subgeneric groupings falling within the generic disclosure also form part of the invention. This includes the generic description of the invention with a proviso or negative limitation removing any subject matter from the genus, regardless of whether or not the excised material is described specifically.

Where features or aspects of the invention are described by reference to a Markush group, the invention also is described thereby in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Although the invention has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

solving the ODE's, for an elapsed time, to determine a concentration of a product of the binding reaction between the probe (P) and the target fragment (P'), wherein the concentration indicates how effectively the probe (P) selectively binds the target fragment (P'), wherein the solved ODE's do not represent (1) binding reactions between the first fragment (A) and the fragment (A') on the target nucleotide sequence (T), (2) binding reactions that are thermodynamically prohibi-

The invention claimed is:

1. A method for synthesizing and using a selected nucleotide probe (P) that selectively binds a target fragment (P') in a target nucleotide sequence (T) in a sample wherein the sample comprises the target nucleotide sequence (T) and a plurality of off-target nucleotide sequences (D) that do not contain the target fragment, wherein the target nucleotide sequence (T) further comprises:
 (1) an off-target fragment on the target nucleotide sequence (O);
 (2) a first fragment (A) that can bind to the target fragment (P'); and
 (3) a second fragment (A') that can bind to the first fragment (A), the method comprising performing, on a suitably programmed computer:

determining a plurality of binding reactions potentially affecting the binding between the probe (P) and the target fragment (P'), which binding reactions comprise those that are
 (i) between the probe (P) and the off-target fragment (O),
 (ii) between the probe (P) and one or more of the off-target nucleotide sequences (D),
 (iii) between the target fragment (P') and the first fragment (A), and
 (iv) between the target fragment (P') and one or more of the off-target nucleotide sequences (D);

calculating one or more kinetic rate for each of the binding reactions;

generating one or more ordinary differential equation (ODE), using at least one of the one or more kinetic rate as a parameter, to represent each of the binding reactions; and tive, or (3) binding reactions involving a nucleotide sequence or fragment in more than one binding reaction at a time;

performing all of the steps for each of a plurality of nucleotide probes;

selecting one or more probes from the plurality of nucleotide probes, the selected one or more probes having among highest concentrations, out of the two or more nucleotide probes, of target fragments that selectively bind the probe over an elapsed time, as determined by the ODE's;

synthesizing the selected probe; and performing binding reactions in a cell or tissue using the synthesized selected probe, the binding reactions being selective to the target fragment with the synthesized selected probe.

2. The method of claim 1, wherein the generation of the equations comprises computing equilibrium rates of the bindings.

3. The method of claim 2, wherein the equilibrium rates are computed with a nearest neighbor algorithm.

4. The method of claim 1, wherein the equations comprise concentrations of one or more of the polynucleotides of the plurality.

5. The method of claim 1, wherein the probe (P) is a primer, a hybridization probe, an siRNA or an antisense polynucleotide.

6. The method of claim 1, wherein the sample is a cell.

7. The method of claim 1, wherein selecting the probe comprises comparing the concentrations of products of the respective binding reactions for at least two of the probes (P).

8. The method of claim 7, wherein the probe (P) having the highest respective concentration is selected.

* * * * *